US00PP30073P2

(12) United States Plant Patent
Hansen

(10) Patent No.: US PP30,073 P2
(45) Date of Patent: Jan. 8, 2019

(54) ***DIANTHUS* PLANT NAMED 'RASPBERRY RUFFLES'**

(50) Latin Name: ***Dianthus* hybrid**
Varietal Denomination: Raspberry Ruffles

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,095

(22) Filed: Feb. 1, 2018

(51) Int. Cl.
*A01H 5/02* (2018.01)

(52) U.S. Cl.
USPC ..... Plt./282
CPC ..... *A01H 5/02* (2013.01)

(58) Field of Classification Search
USPC ..... Plt./282, 277
CPC ..... A01H 5/02
See application file for complete search history.

*Primary Examiner* — Kent L Bell

(57) ABSTRACT

A new and unique plant cultivar of perennial carnation or pinks, *Dianthus* plant named 'Raspberry Ruffles' with numerous, large, fully-double, lightly-fragrant flowers producing a rounded full face. Individual flowers can have about 114 petals with irregularly toothed margins and raspberry coloration toward the middle and light pink to white margins. The numerous stems cover the top of the plant with flowers for about six weeks. The habit is compact with long, thin, blue-green foliage.

1 Drawing Sheet

Botanical denomination: *Dianthus* hybrid.
Cultivar designation: 'Raspberry Ruffles'.

BACKGROUND OF THE INVENTION

The present invention relates to the new and distinct cultivar of carnation or pinks from the genus *Dianthus* and given the cultivar name 'Raspberry Ruffles'. The new plant was the result of an intentional cross on May 14, 2012 under the direction of the inventor between *Dianthus* 'WP Passion' U.S. Plant Pat. No. 20,440 as the female or seed parent and 'Valda Isolde' U.S. Plant Pat. No. 13,915 (known by the tradename Fancy Knickers) as the male or pollen parent. The cross was harvested and sown on Jul. 2, 2012. The new hybrid was first isolated from trials at a wholesale perennial nursery in Zeeland, Mich. during the summer of 2013 as a single seedling clone and given the breeder number 12-64-3 later in the evaluation processes. *Dianthus* 'Raspberry Ruffles' has been asexually propagated at the same nursery in Zeeland, Mich. since 2013 using traditional shoot tip cutting procedures and found to reproduce plants that are identical and exhibit all the characteristics of the original plant.

No plants of *Dianthus* 'Raspberry Ruffles' have been sold in this country, or anywhere in the world, under this or any name or tradename, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

*Dianthus* 'Raspberry Ruffles' has not been evaluated under all possible environmental conditions. The phenotype may vary with variations in environment including: growing temperature, available sunlight, nutrients, water, etc. without a change in the genotype of the plant.

Compared with the new plant, the female parent 'WP Passion' has red flowers without bar or band, that have less than one-third the number of petals per flower and the petals have an entire to sinuate margin compared to the crenate to dentate margins of 'Raspberry Ruffles'. The male parent, 'Fancy Knickers', has white flower petals with a magenta base compared with the raspberry-colored petals with lighter margin of the new plant with up to 100 more petals per flower. The nearest comparison cultivars known to the inventor are: 'Cherry Vanilla' U.S. Plant Pat. No. 29,684 and 'Coral Reef' U.S. Plant Pat. No. 19,660. The flower petals of 'Coral Reef' are primarily a lighter reddish coral color and a wide white margin with fewer petals than the new plant. Compared with 'Cherry Vanilla', a sister sibling, the ground flower petal color is a deeper red and the margin is broader and more contrasting. Compared with 'Cranberry Cocktail' U.S. Plant Pat. No. 28,603 the comparison has solid hot magenta pink flowers with about half the number of petals per flower and without a lighter margin on the petals.

*Dianthus* 'Raspberry Ruffles' is distinct from its parents and all other *Dianthus* known to the applicant in the following combined traits:

1. Fully-double flowers opening up with petal counts per flower about 105.
2. Petals having a raspberry coloration with thin margin beginning light pink and becoming white.
3. Petal margin irregularly toothed.
4. Typically two flowers per stiff, upright peduncle.
5. Large flowers producing a lightly-sweet spicy fragrance.
6. Flower near top of clump, vigorous, with compact habit and finely-textured blue-green foliage.

BRIEF DESCRIPTION OF THE DRAWINGS

The photographs of the new invention are of a two-year-old plant grown in full-sun trial garden and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
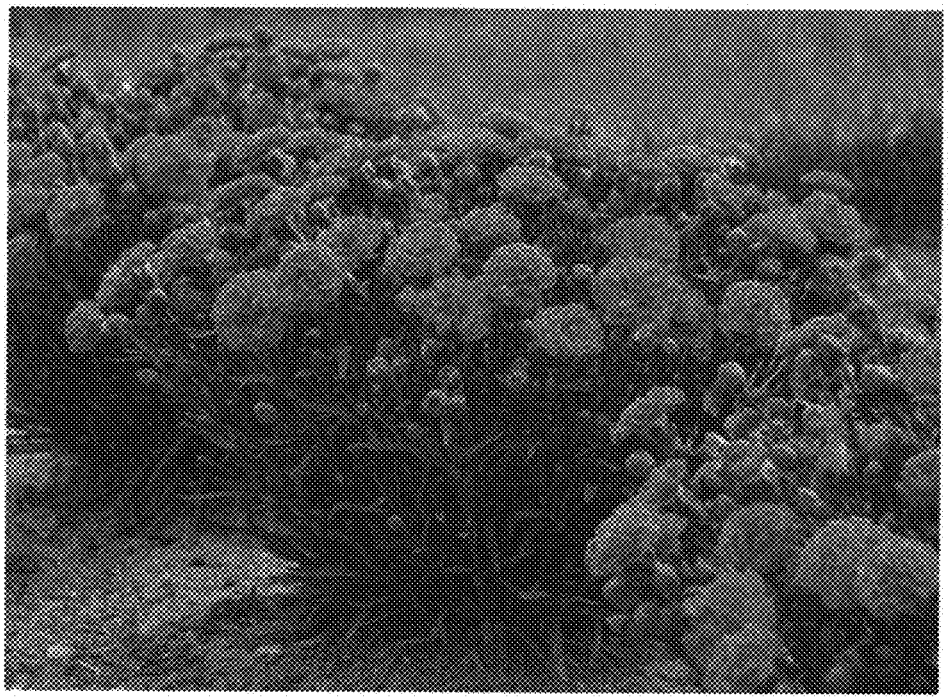
FIG. 1 shows the habit of the plant in mid-season flowering.
Figure 2:
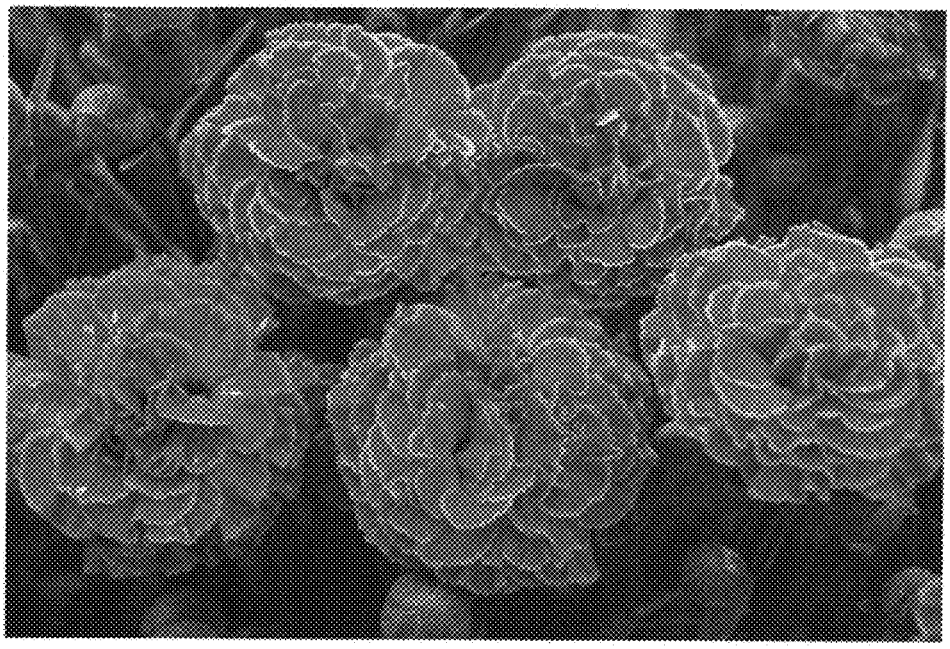
FIG. 2 shows a close-up of the flowers and bud.

The following detailed description of the new plant is based on observations of two-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: *Dianthus* 'WP Passion' as the female or seed parent and *Dianthus* 'Fancy Knickers' as the male or pollen parent;

Plant habit: Caespitose, herbaceous, evergreen, winter-hardy perennial; stems and peduncles branched, mostly erect stems; height of foliage about 12.0 cm and about 38.0 cm across; height in flower is about 33.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute apex; base decurrent, adpressed along stem to slightly perfoliate; no fragrance detected.

*Leaf dimensions*.—To about 11.0 cm long and about 7.0 mm wide, average about 7.2 cm long and 5.5 mm wide.

*Leaf color*.—Young expanding leaves abaxial between RHS 138A and RHS 138B and adaxial nearest RHS 138A; mature abaxial nearest RHS N138A and adaxial blend between RHS N138A and RHS 139A.

*Venation*.—Not pronounced; obscurely pinnate, coloration same as that of leaf top and bottom.

Stems: About 60 per plant; upright; terete, glabrous, glaucous; solid; branching in upper nodes;

*Stem size*.—About 6.0 cm long to peduncle and about 3.0 mm diameter at base.

*Stem color*.—Between RHS N138A and RHS 139A.

*Branching*.—Lightly branched; typically alternate from lower nodes; about 2 per main stem and about 120 per plant; branch size average about 15.0 cm long and 2.5 mm diameter at time of initial flowering.

*Nodes*.—About 3.5 mm across; color nearest RHS 145D.

*Internodes*.—About 9 per stem before peduncle; average about 3.3 cm apart depending on growing temperature, shorter in cooler conditions.

Inflorescence:

*Type*.—Terminal, cymose; perfect; salverform; actinomophic; fully double.

*Attitude*.—Mostly upright to slightly outward around perimeter of plant.

*Dimension*.—About 7.5 cm across and extending about 5.8 cm above base of calyx tube and 2.4 cm wide at apex of calyces.

*Flowers per stem*.—Up to 4, average 2.

*Pedicel*.—Glaucous, glabrous, terete, stiff; primarily upright.

*Pedicel size*.—Terminal flower about 2.0 cm long and about 2.5 mm diameter; other flowers average about 2.5 cm long and 2.0 mm diameter.

*Pedicel color*.—Blend between RHS 122A and RHS 189B.

*Flower bud*.—Slowly opening; glabrous; glaucous; with calyx still closed: ellipsoid with rounded base and rounded to obtuse apex; about 2.2 cm long and 2.0 cm across at distal fusion point of sepals; with petals extended beyond calyx and still parallel to calyx side: terete, with rounded base and truncate apex or petal tops, about 3.3 cm long and 2.5 cm across near apices of sepals.

*Flower bud color*.—With petals enclosed in calyx distally nearest RHS 138A with strong tinting of blend between RHS 187B and RHS N187A in high light exposure, mid portion nearest RHS 138B with an irregular horizontal band strongly tinted with a blend of RHS 187B and RHS N187A with high light exposure, base between RHS 139D and RHS 138B; with petals extended beyond calyx petal portion between RHS 64B, RHS 64C and RHS 63A.

*Flower period*.—Beginning late spring and continuing for about six weeks.

*Flower fragrance*.—Light, sweet spicy, clove-like.

*Flower lasting quality*.—Individually about 6 to 8 days on or cut from plant.

*Petals*.—Glabrous; up to about 114 per flower, average about 105 in terminal flowers and average 78 in axillary flowers; consisting of a rounded blade or limb and a claw; limb and claw combined are flabellate; limb apex and distal margin crenate and repand with irregular dentations average 1.0 mm wide and 1.0 mm long, basal limb and claw entire; limb of inner petals folded longitudinally to nearly a 90 degree angle along distal one-third of center with sides toward abaxial surface; persistent.

*Petal dimensions*.—Whole petal to about 44.0 mm long and 27.0 mm across at limb, average about 40.0 mm long and about 19.0 mm wide at limb; claw tapering to attenuate base of about 1.0 mm across.

*Petal color*.—Young abaxial claw nearest RHS 145D, young abaxial limb base lighter than RHS 65D and distal half between RHS 63B and RHS 63A; young adaxial claw nearest RHS 145C, young adaxial limb base center nearest RHS 145D, young adaxial limb perimeter and basal perimeter between RHS 67B and RHS 67C with center limb ground a blotchy bar between RHS 61A and RHS 61B; mature abaxial claw nearest RHS 145C, mature abaxial limb base lighter than RHS 65D and limb distal half between RHS 64C and RHS 64D; mature adaxial claw nearest RHS 145C, adaxial limb base center nearest RHS 145D and limb perimeter nearest RHS 73A and wide center ground nearest RHS 61B.

*Calyx*.—Glabrous; glaucous abaxial; margins entire to micro-ciliolate; consisting of five sepals with acute apex and fused base forming five-toothed campanulate corolla tube fused in about proximal 12.0 mm;

frequently with one joint between sepals split nearly to base; campanulate to about 22.0 mm long and about 20.0 mm in diameter at apex.

*Sepals*.—Five; individually about 22.0 mm long and about 12.0 mm across at distal fusion.

*Sepal color*.—Abaxial margin between RHS 165A and RHS 165B, base nearest RHS 145A and terminal 18 mm nearest RHS 137A with strong tinting of between RHS 187B and RHS N187A with intense light; adaxial margin between RHS 165A and RHS 165B, mid-portion and base nearest RHS 145C.

*Peduncle*.—Glabrous, glaucous, terete, stiff; about 15.0 cm long and about 3.0 mm diameter at base; attitude mostly upright.

*Peduncle color*.—Blend between RHS 122A and RHS 189B.

*Epicalyx*.—Two sets of three subtending each flower adpressed calyces; glaucous, glabrous; sessile; margin entire; outer set broadly lanceolate with broadly acute apex and cuneate base, about 11.0 mm long and about 6.0 mm wide; inner set deltoid with acute apex and truncate base, about 10.0 mm long and about 15.0 mm across.

*Epicalyx color*.—Both sets abaxial base nearest RHS 146D, mid-portion nearest RHS 135A and RHS 137A, margin translucent to nearest RHS 158D; adaxial base nearest RHS 146D, mid-portion nearest RHS 135A, margin translucent to nearest RHS 158D.

*Androecium*.—About 10; most rudimentary. Filaments: to 27 mm long and 0.5 mm diameter, average about 11.0 mm long and 0.3 mm diameter; color base nearest RHS 155D becoming nearest RHS 64A in terminal 5.0 mm. Anthers: rare, typically rudimentary; when present dorsifixed; to 3.5 mm long and 1.5 mm across; color between RHS 70A and RHS 71A. Pollen: rare; color nearest RHS 201C when developed.

*Gynoecium*.—Two or three; to 2.5 cm long. Pistil: two to three; to about 16.5 mm long. Style: bifurcate or trifurcate just above ovary; puberulent adaxial; to 14.0 mm long and 1.0 mm across; color nearest RHS 71A proximally and nearest RHS NN155D toward base. Stigma: split in terminal 1.5 mm; puberulent; about 2.5 mm long and 1.0 mm wide; color darker than RHS 71A. Ovary: superior; ellipsoid-shaped with broadly acute flared apex and truncate base; about 9.0 mm long and 10.0 mm wide toward flared apex; color nearest RHS 144A distally and nearest RHS 145A proximally.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Raspberry Ruffles' essentially as herein described and illustrated.

* * * * *